United States Patent [19]
Smith et al.

[11] Patent Number: 5,492,304
[45] Date of Patent: Feb. 20, 1996

[54] SEAL ASSEMBLY FOR ACCOMMODATING INTRODUCTION OF SURGICAL INSTRUMENTS

[75] Inventors: Robert C. Smith, Watertown; Richard D. Gresham, Monroe, both of Conn.

[73] Assignee: United States Surgical Corporation, Norwalk, Conn.

[21] Appl. No.: 80,465

[22] Filed: Jun. 16, 1993

[51] Int. Cl.⁶ .......................... F16L 37/28; A61M 5/178
[52] U.S. Cl. ...................... 251/149.1; 251/342; 604/167; 604/256
[58] Field of Search .................................. 606/184, 185; 604/167, 256, 164, 171; 251/149.1, 342

[56] References Cited

U.S. PATENT DOCUMENTS

| | | |
|---|---|---|
| 729,423 | 5/1903 | Scheiber et al. . |
| 2,797,837 | 7/1957 | Roberts . |
| 3,086,797 | 4/1963 | Webb . |
| 3,197,173 | 7/1965 | Taubenbeim . |
| 3,438,607 | 4/1969 | Williams et al. . |
| 3,766,916 | 10/1973 | Moorehead et al. . |
| 3,811,440 | 5/1974 | Moorehead et al. . |
| 3,856,010 | 12/1974 | Moorehead et al. . |
| 3,875,938 | 4/1975 | Mellor . |
| 3,920,215 | 11/1975 | Knauf . |
| 3,970,089 | 7/1976 | Saice . |
| 3,977,400 | 8/1976 | Moorehead . |
| 3,994,287 | 11/1976 | Turp et al. . |
| 4,000,739 | 1/1977 | Stevens . |
| 4,056,116 | 11/1977 | Carter et al. ............... 251/342 |
| 4,136,694 | 1/1979 | Kuehn ........................ 251/342 |
| 4,149,535 | 4/1979 | Volder . |
| 4,177,814 | 12/1979 | Knepshield . |
| 4,231,400 | 11/1980 | Friedling et al. . |
| 4,240,411 | 12/1980 | Hosono . |
| 4,243,034 | 1/1981 | Brandt . |
| 4,324,239 | 4/1982 | Gordon et al. . |
| 4,378,013 | 3/1983 | LeFevre . |
| 4,424,833 | 1/1984 | Spector et al. . |
| 4,430,081 | 2/1984 | Timmermans . |
| 4,436,519 | 3/1984 | O'Neill . |
| 4,447,237 | 5/1984 | Frisch et al. . |
| 4,473,369 | 9/1984 | Lueders et al. . |
| 4,475,548 | 10/1984 | Muto . |
| 4,496,348 | 1/1985 | Genese et al. . |
| 4,535,773 | 8/1985 | Yoon . |
| 4,580,573 | 4/1986 | Quinn . |
| 4,610,665 | 9/1986 | Matsumoto et al. . |
| 4,610,674 | 9/1986 | Suzuki et al. . |
| 4,626,245 | 12/1986 | Weinstein . |
| 4,634,421 | 1/1987 | Hegemann . |
| 4,654,030 | 3/1987 | Moll et al. . |
| 4,655,752 | 4/1987 | Honkanen et al. . |
| 4,673,393 | 6/1987 | Suzuki et al. . |
| 4,723,550 | 2/1988 | Bales et al. . |
| 4,786,028 | 11/1988 | Hammond . |

(List continued on next page.)

FOREIGN PATENT DOCUMENTS

| | | |
|---|---|---|
| 0344907 | 6/1989 | European Pat. Off. . |
| 0350291 | 1/1990 | European Pat. Off. . |
| 2019219 | 10/1979 | United Kingdom . |
| 2065479 | 7/1981 | United Kingdom . |
| 9301850 | 2/1993 | WIPO . |

*Primary Examiner*—A. Michael Chambers

[57] ABSTRACT

A seal assembly is provided which includes a housing and resilient first seal means associated with the housing. The first seal means is preferably a gasket having an aperture formed therein for receiving surgical instrumentation adapted to cooperate with a dilating means having an exterior face associated with the housing for dilating the aperture of the gasket. The first seal means and the dilating means are adapted for relative movement therebetween, the first seal means and the dilating means assuming a first position wherein the aperture of the first seal means is spaced from the dilating means and is adapted to receive surgical instrumentation of a first diameter with minimal insertion force, and assuming a second position wherein the aperture of the first seal means is stretched around the exterior face of the dilating means for receiving surgical instrumentation of a second diameter greater than the first diameter with minimal insertion force.

22 Claims, 13 Drawing Sheets

U.S. PATENT DOCUMENTS

| | | |
|---|---|---|
| 4,798,594 | 1/1989 | Hillstead . |
| 4,817,631 | 4/1989 | Schnepp-Pesch et al. . |
| 4,839,471 | 6/1989 | Clark et al. . |
| 4,842,591 | 6/1989 | Luther . |
| 4,869,717 | 9/1989 | Adair . |
| 4,874,377 | 10/1989 | Newgard et al. . |
| 4,895,346 | 1/1990 | Steigerwald . |
| 4,895,565 | 1/1990 | Hillstead . |
| 4,909,798 | 3/1990 | Fleischhacker et al. . |
| 4,917,668 | 4/1990 | Haindl . |
| 4,929,235 | 5/1990 | Merry et al. . |
| 4,960,259 | 10/1990 | Sunnanväder et al. . |
| 4,960,412 | 10/1990 | Fink . |
| 4,978,341 | 12/1990 | Niederhauser . |
| 5,000,745 | 3/1991 | Guest et al. . |
| 5,009,391 | 4/1991 | Steigerwald . |
| 5,009,643 | 4/1991 | Reich et al. . |
| 5,041,095 | 8/1991 | Littrell . |
| 5,053,014 | 10/1991 | Van Heugten . |
| 5,053,016 | 10/1991 | Lander . |
| 5,064,416 | 11/1991 | Newgard et al. . |
| 5,069,424 | 12/1991 | Dennany et al. ............... 251/149.1 |
| 5,104,383 | 4/1992 | Shichman . |
| 5,104,389 | 4/1992 | Deem et al. . |
| 5,127,626 | 7/1992 | Hilal et al. . |
| 5,127,909 | 7/1992 | Shichman . |
| 5,167,636 | 12/1992 | Clement . |
| 5,195,980 | 3/1993 | Catlin . |
| 5,215,538 | 6/1993 | Larkin ............... 251/149.1 |
| 5,226,891 | 7/1993 | Bushatz et al. . |
| 5,308,336 | 5/1994 | Hart et al. ............... 604/256 |
| 5,330,437 | 7/1994 | Durman ............... 604/167 |
| 5,350,364 | 9/1994 | Stephens ............... 604/256 |
| 5,385,553 | 1/1995 | Hart et al. ............... 604/256 |
| 5,395,342 | 3/1995 | Yoon . |

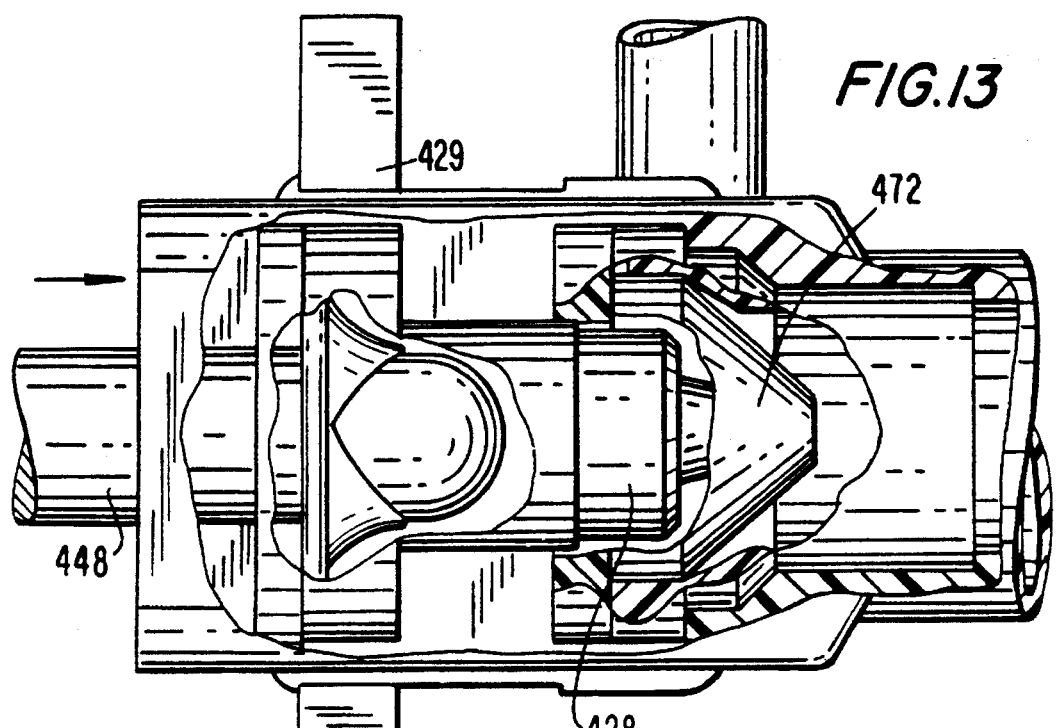
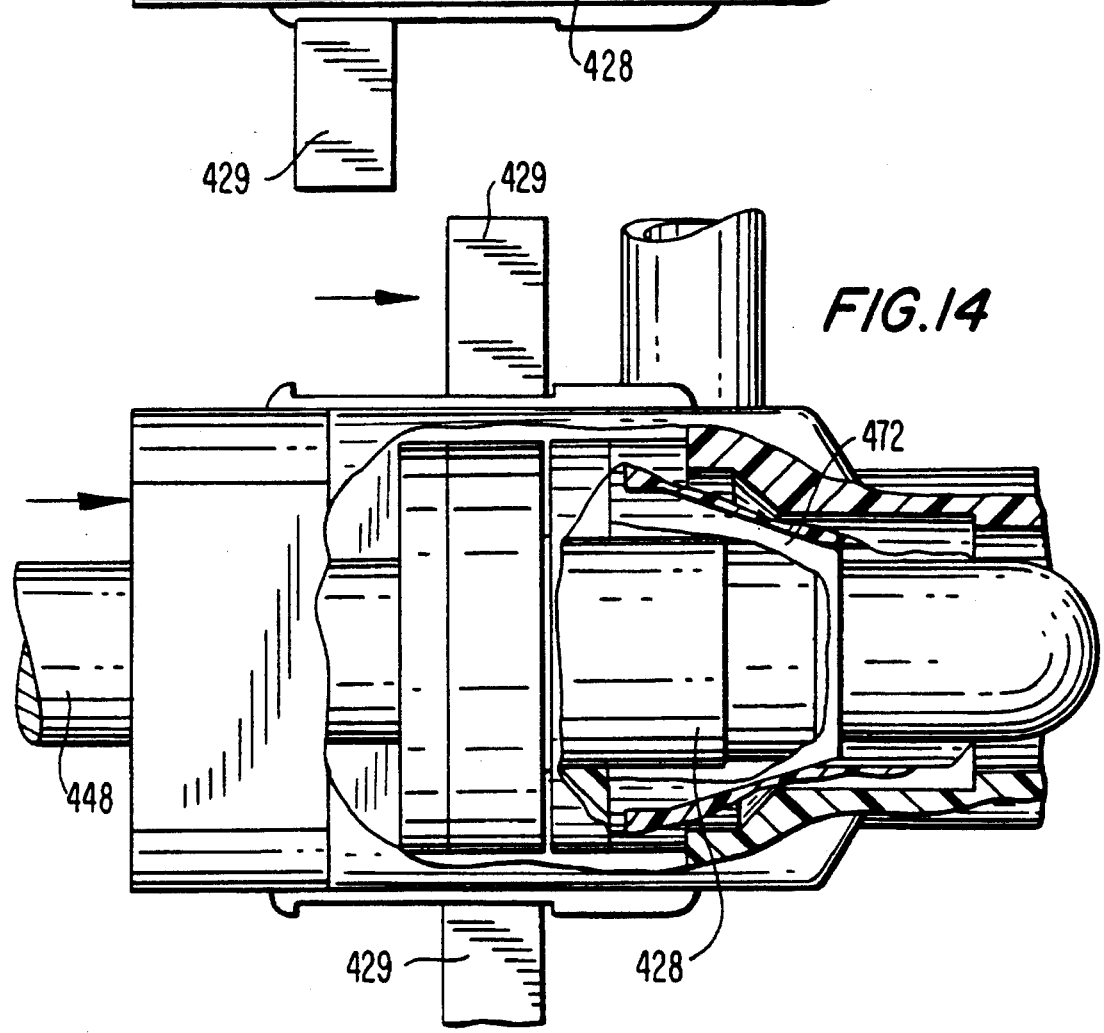

SEAL ASSEMBLY FOR ACCOMMODATING INTRODUCTION OF SURGICAL INSTRUMENTS

BACKGROUND OF THE INVENTION

1. Field of the Invention

This invention relates to seal systems which are adapted to allow the introduction of surgical instrumentation into a patient's body. In particular, the invention is applicable to a cannula assembly wherein a cannula housing includes or is adapted to receive a seal assembly to sealingly accommodate instruments of different diameters inserted through the seal assembly and cannula.

2. Description of the Related Art

In laparoscopic procedures surgery is performed in the interior of the abdomen through a small incision; in endoscopic procedures surgery is performed in any hollow viscus of the body through narrow tubes or cannula inserted through a small entrance incision in the skin. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. Moreover, laparoscopic and endoscopic procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a trocar assembly comprised of a cannula assembly and an obturator assembly. Since the cannula assembly provides a direct passage for surgical instrumentation from outside the patient's body to access internal organs and tissue, it is important that the cannula assembly maintain a relatively gas-tight interface between the abdominal cavity and the outside atmosphere. The cannula assembly thus generally includes a cannula attached to a cannula housing: containing a seal assembly adapted to maintain a seal across the opening of the cannula housing.

Since surgical procedures in the abdominal cavity of the body require insufflating gases to raise the cavity wall away from vital organs, the procedure is usually initiated by use of a Verres needle through which a gas such as CO2 is introduced into the body cavity, thereby creating a pneumoperitoneum. Thereafter, the pointed obturator of the obturator assembly is inserted into the cannula assembly and used to puncture the abdominal wall. The gas provides a positive pressure which raises the inner body wall away from internal organs, thereby providing the surgeon with a region within which to operate and avoiding unnecessary contact with the organs by the instruments inserted through the cannula assembly. Following removal of the obturator assembly from the cannula assembly, laparoscopic or endoscopic surgical instruments may be inserted through the cannula assembly to perform surgery within the abdominal cavity.

Without the obturator assembly to block the flow of insufflation gas out from the cavity, other structure must be provided to maintain a relatively fluid-tight interface between the abdominal cavity and the outside atmosphere. Generally in the context of insufflatory surgical procedures, there are two sealing requirements for cannula assemblies. The first requirement is to provide a substantially fluid-tight seal when an instrument is not being introduced into or is not already present in the cannula. The second requirement is to provide a substantially fluid-tight seal when an instrument is being introduced into or is already present in the cannula. Additionally, as endoscopic and laparoscopic surgical procedures and techniques have advanced, it has become desirable to accommodate surgical instrumentation of varying outside diameters through a single cannula assembly in a given surgical procedure, thereby minimizing the number of cannulae required and facilitating efficiency in the surgical procedure.

To meet the first sealing requirement, various seals have been provided for maintaining the pneumoperitoneum in the cavity when no trocar or other surgical instrument is present in the cannula. For example, a pivotally mounted flapper valve may be provided which pivots open upon insertion of an instrument and pivots closed, under a spring bias, once the instrument is removed. Conventional flapper valves may also be manually opened by pivoting a lever provided on the exterior of the housing. An example of such a flapper valve is disclosed in U.S. Pat. No. 4,943,280 to Lander. Trumpet valves are also well known for use in sealing a cannula assembly in the absence of a surgical instrument U.S. Pat. No. 4,655,752 to Honkanen et al. discloses a cannula including a housing and first and second seal members. The first seal member is conically tapered towards the bottom of the housing and has a circular opening in its center, while the second seal member is cup-shaped. The second seal member includes at least one slit to allow for passage of instruments.

U.S. Pat. No. 4,929,235 to Merry et al. discloses a self-sealing catheter introducer having a sealing mechanism to prevent blood or fluid leakage that includes a planar sealing element having a slit, and a conical sealing element proximal of the planar sealing element so that if the distal planar sealing element is moved proximally it rests upon the conical sealing element, each sealing element being adapted to surround a tube.

U.S. Pat. Nos. 4,874,377 and 5,064,416 to Newgard et al. relate to a self-occluding intravascular cannula assembly in which an elastomeric valving member is positioned transversely to a housing and is peripherally compressed to cause displacement, distortion and/or rheological flow of the elastomeric material. A frustoconical dilator projection is provided which cooperates with the elastomeric valving member in moving the valving member to a non-occluding position.

U.S. Pat. No. 5,104,3838 to Shichman relates to a trocar adapter seal which is adapted to be associated with a cannula assembly and which advantageously reduces the diameter of the cannula assembly to accommodate instruments of smaller diameter. The trocar adapter seal may be removed from the cannula assembly so that the cannula assembly may once again accommodate instruments of larger diameter. WO 93/04717 to Mudler et al. describes a similar trocar adapter seal system in which a pair of seal adapter plates are slidably mounted to the cannula housing and may be selectively positioned transverse the cannula housing aperture for accommodating surgical instrumentation therethrough.

Cannula assemblies have also been developed which are provided with a series of resilient sealing elements having a central aperture, e.g., commonly assigned, co-pending applications Ser. No. 07/874,291 filed Apr. 24, 1992 and Ser. No. 07/873,416 filed Apr. 24, 1992 both abandoned. Upon insertion of an instrument, the sealing elements resiliently receive the instrument, while maintaining a seal around the instrument across a range of instrument diameters, e.g., 5 to 12 mm. Upon withdrawal of the instrument, a fluid-tight seal is provided by the internal sealing elements.

Although attempts have been made to provide a seal assembly as part of or for use in conjunction with a cannula assembly which maintains the integrity of the seal between the body cavity and the atmosphere outside the patient's body, seal systems provided to date have failed to address the full range of surgeons' needs, especially when it is desired to utilize different instruments having different diameters therethrough.

SUMMARY OF THE INVENTION

The present invention provides a seal assembly which will allow a surgeon to efficaciously utilize instruments of varying diameter in a surgical procedure. The seal assembly of the invention obviates the need for multiple adapters to accommodate instruments of varying diameter by providing a dilating funnel which is adapted to spread open the aperture of a seal member, thereby allowing the seal member to receive larger instrumentation with minimal force required on the part of the user.

In accordance with the present invention a seal assembly is provided which comprises a housing and resilient first seal means associated with the housing, the first seal means having an aperture formed therein for receiving surgical instrumentation. In one embodiment, the first seal means is a substantially planar, resilient gasket that is mounted transverse with respect to the housing. The seal assembly further includes dilating means associated with the housing for dilating the aperture of the first seal means. The first seal means and the dilating means are adapted for relative movement therebetween, such that the first seal means and the dilating means assume a first position wherein the aperture of the first seal means is spaced from the dilating means and is adapted to receive surgical instrumentation of a first diameter with minimal insertion force, i.e., less than about 2 lbs. and preferably less than about 1 lb., and assume a second position wherein the aperture of the first seal means is stretched around the exterior face of the dilating means for receiving surgical instrumentation of a second diameter greater than the first diameter with minimal insertion force, i.e., less than about 2 lbs. and preferably less than about 1 lb.

Preferably, the housing is adapted to be associated with a cannula assembly which includes a cannula housing and a tubular cannula. The cannula assembly may include a second seal means positioned within the cannula housing, such second seal means preferably comprising a distally directed duckbill member. The second seal means may also comprise a second substantially planar, resilient gasket that is mounted transverse with respect to the cannula housing, the aperture of the second resilient gasket being of larger diameter than the aperture of the resilient gasket found in the sealing assembly. The second seal means preferably provides a substantially fluid-tight seal in the absence of a surgical instrument passed therethrough. This substantial fluid-tight seal need only be provided, however, when the cannula assembly is introduced to an insufflated body cavity, in which case the positive pressure within the body cavity may force the distal faces of the preferred duckbill member into sealing abutment with each other.

The housing of the seal assembly of the invention may comprise a bellows structure which is adapted to assume an extended position which corresponds to the first position of the first seal means and the dilating means, and a collapsed position which corresponds to the second position of the first seal means and the dilating means. The bellows structure may be encased within a rigid outer frame which defines a constant axial dimension for the seal assembly of the invention or, in the absence of such outer frame, movement of the bellows structure to the collapsed position may reduce the overall axial dimension of the seal assembly. The seal assembly may further comprise a flange associated with the bellows structure for moving the bellows structure between the extended position and the collapsed position. Biasing means, e.g., a spring, may be provided for biasing the bellows structure to the extended position. Alternatively, the resilience of the material from which the bellows structure and/or the first sealing means are fabricated may serve to bias the bellows structure to the extended position. A vent may also be provided between the interior of the bellows structure and the dilating means such that air within the bellows structure has a path of egress when the bellows structure is collapsed. To prevent unacceptable gas leakage from the insufflated body cavity when such vent is provided, the bellows structure preferably cooperates with adjoining structures to define a substantially fluid-fight region, with the exception of the vent described above.

As noted above, the second seal means positioned within the cannula assembly may include a substantially planar gasket. This gasket is preferably positioned proximal the distally directed duckbill member. In such case, the dilating means may include a proximally directed dilating funnel for spreading the gasket associated with the seal assembly of the invention and a distally directed member which is adapted to contact and expand the planar gasket of the second seal means for efficacious receipt of surgical instrumentation therethrough.

BRIEF DESCRIPTION OF THE DRAWINGS

The foregoing features of the present invention will become more readily apparent and will be better understood by referring to the following detailed description of preferred embodiments of the invention, which are described hereinbelow with reference to the drawings wherein:

FIG. 5A is an exploded view with pans separated of a portion of a cannula assembly which is adapted to be associated with the seal assembly of FIG. 5;

FIGS. 13 and 14 are progressive partial cross-sectional views of the embodiment of the seal assembly of FIG. 12, which show the operation of the seal assembly as a surgical instrument is inserted therein.

DETAILED DESCRIPTION OF THE PREFERRED EMBODIMENTS

The present invention contemplates the use of all types of endoscopic and laparoscopic surgical instruments therethrough including, but not limited to, clip appliers, surgical staplers, lasers, endoscopes, laparoscopes, forceps, photographic devices, graspers, dissectors, suturing devices, scissors, and the like. All of such devices, are referred to herein as "instruments".

The seal assembly of the present invention, either alone or in combination with a seal system internal to a cannula assembly, provides a substantial seal between a body cavity of a patient and the outside atmosphere before, during and after insertion of an instrument through the cannula assembly. Moreover, the seal assembly of the present invention is capable of accommodating instruments of varying diameters, e.g., from 5 mm to 15 mm, by providing a gas tight seal with each instrument when inserted. The :flexibility of the present seal assembly greatly facilitates endoscopic surgery where a variety of instruments having differing diameters are often needed during a single surgical procedure.

Figure 1:
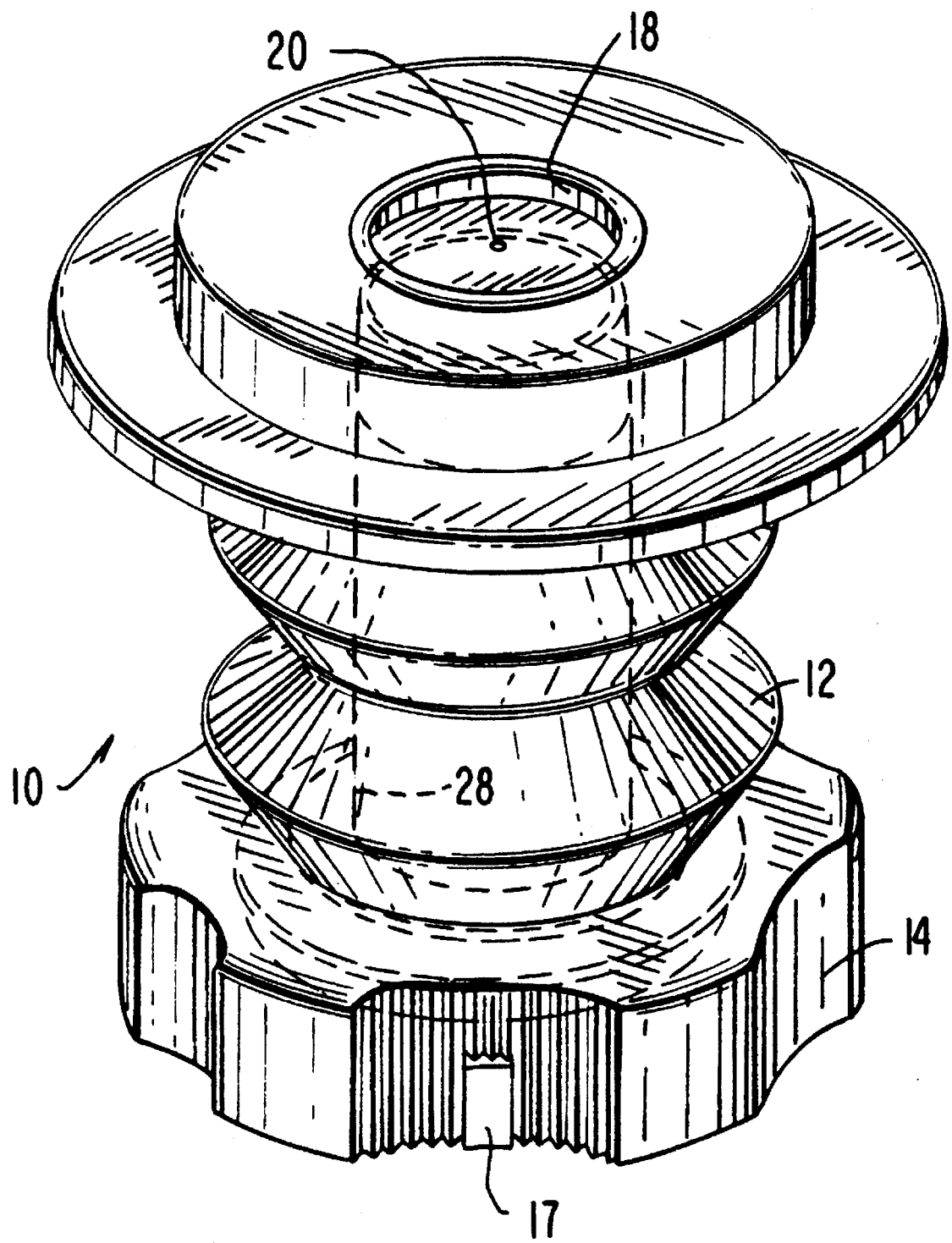
FIG. 1 is a perspective view of one embodiment of the seal assembly of the present invention.

Referring to the drawings, in which like reference numerals identify identical or similar elements, FIGS. 1–4 illustrate a preferred embodiment of the seal assembly of the present invention. Referring initially to FIG. 1 in conjunction with FIGS. 2 and 2A, seal assembly 10 includes a housing in the form of bellows 12 having knurled collar 14 attached thereto by any suitable means such as adhesives, heat welding, etc. Bellows 12 is fabricated from a resilient material, e.g., isoprene, to facilitate the movements described hereinbelow and is preferably about 1 to about 4 cm in axial dimension when at rest.

Knurled collar 14 serves to adapt bellows 12 for removable attachment to cannula assembly 16. In a preferred embodiment of the invention, seal assembly 10 is detachably mounted to cannula assembly 16 through a bayonet attachment, and knurled collar 14 facilitates the rotation of seal assembly 10 relative to cannula assembly 16 in effectuating the bayonet attachment. Printed indicia 17 and 17A assist the surgeon in aligning knurled collar 14 with cannula assembly 16 and inclined cam surface 45 guides an internal projection (not pictured) on knurled collar 14 to fiat 47, whereby seal assembly 10 is detachably mounted to cannula assembly 16. Preferably, cannula assembly 16 includes a second inclined cam surface and flat on the opposite side thereof to cooperate with a second internal projection on knurled collar 14 to provide optimum stability to the interface between cannula assembly 16 and seal assembly 10. However, any suitable attaching means may be utilized, such as, for example, any quick connect mechanism.

Seal assembly 10 further includes a first seal means, such as gasket 18, which is preferably fabricated from a resilient elastomeric material, e.g., isoprene. Gasket 18 is provided with aperture 20 formed centrally therethrough and preferably includes a proximally directed convolution which increase the flexibility and resilience thereof. Aperture 20 is preferably on the order of 4.5 mm in diameter so that aperture 20 has a diameter which is less than the smallest diameter instrument which is likely to be utilized therethrough during the course of an endoscopic surgical procedure. Gasket 18 is securely affixed to bellows 12 so as to form a fluid tight seal along periphery 22. Alternatively, gasket 18 may be formed integrally with bellows 12 by known manufacturing processes, e.g., injection molding.

Seal assembly 10 may also include additional sealing structures, such as gasket member 24, which may serve a variety of purposes. For example, gasket member 24 may simply function as a washer to ensure that seal assembly 10 is internally sealed. Alternatively, gasket member 24 may serve to sea Jingly engage instruments inserted through seal assembly 10 when aperture 20 of gasket 18 is stretched around the exterior face of dilator 28, as discussed below. Gasket member 24 is also preferably fabricated from a resilient elastomeric material, e.g., isoprene. An aperture 26 is formed through the center of gasket member 24 having a greater diameter than the diameter of aperture 20 in gasket 18. For example, if gasket member 24 is intended to sealing engage instruments passed therethrough and if aperture 20 is on the order of 4.5 mm, aperture 26 is preferably on the order of 9 to 10 mm. In this way, gasket 24 will sealingly engage surgical instruments which are inserted through seal assembly 10 having a diameter of 9 mm and greater.

Seal assembly 10 further includes dilating means such as dilator 28 which is preferably made of a rigid polymeric material, e.g., ABS (acrylonitrile-butadiene-styrene) or a suitable polycarbonate material. Dilator 28 has a passageway 30 formed therein which allows for passage of instruments therethrough. Flange 32 is formed at distal end- 34 of dilator 28 and is configured and dimensioned for attachment to knurled collar 14, e.g., by an appropriate adhesive, sonic welding or the like. Inner wall 33 of dilator 28 is preferably of substantially uniform diameter, whereas the outer face 35 of dilator 28 preferably includes an inwardly tapered portion 39 at its proximal end. Inwardly tapered portion 39 facilitates interaction of dilator 28 with gasket 18 when dilator 28 acts to spread aperture 20 thereof. The inner diameter of dilator 28 is selected to accommodate free passage of the instrumentation to be used therethrough and is typically on the order of 13 to 14 mm. Different internal diameters may be selected, however, based on the instrumentation seal assembly 10 is intended to accommodate. Dilator 28 also optionally includes vent 29 which permits gas communication therethrough. Vent 29 facilitates the collapse of bellows 12, as discussed below, by providing a path of egress for the air located between outer face 35 of dilator 28 and bellows 12. Optionally, a plurality of vents may be circumferentially and/or axially spaced around dilator 28 to facilitate such air egress.

Figures 2, 2A:
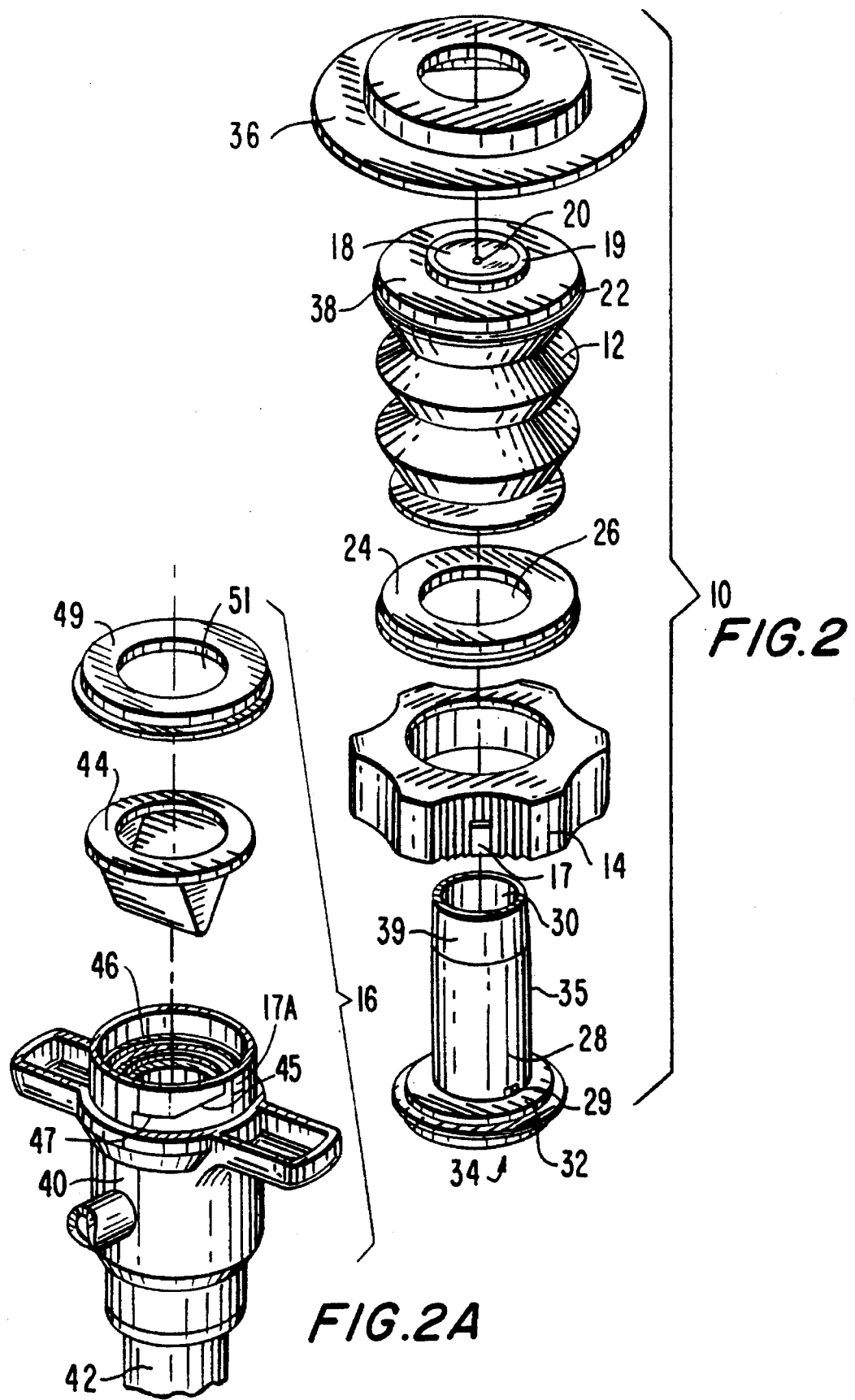
FIG. 2 is an exploded view with parts separated of the embodiment of FIG. 1.
FIG. 2A is an exploded view with parts separated of a portion of a cannula assembly which is adapted to be associated with the seal assembly of FIG. 2.

Referring to FIG. 2A, cannula assembly 16 includes cannula housing 40 and cannula 42 which is attached thereto and which extends distally therefrom. Cannula assembly 16 preferably includes a second seal means, such as distally directed duckbill 44 mounted in interior region 46 of cannula housing 40. Duckbill 44 provides a substantially fluid-tight seal when communicating with an insufflated body cavity to substantially prevent escape of gases and fluids from inside the body cavity when no instrument is present in cannula assembly 16. Cannula assembly 16 also preferably includes a second gasket 49 fabricated from a resilient elastomeric material, e.g., isoprene. Second gasket 49 is provided with aperture 51 formed centrally therethrough. The diameter of aperture 51 may range widely, e.g. from 3 mm to 15 mm, based on the diameter of cannula 42 which defines the instrument sizes cannula assembly 16 is generally intended to accommodate. Depending on the diameter of aperture 51, second gasket 49 is adapted to sealingly engage surgical instruments of greater diameter with respect thereto.

Figure 3:
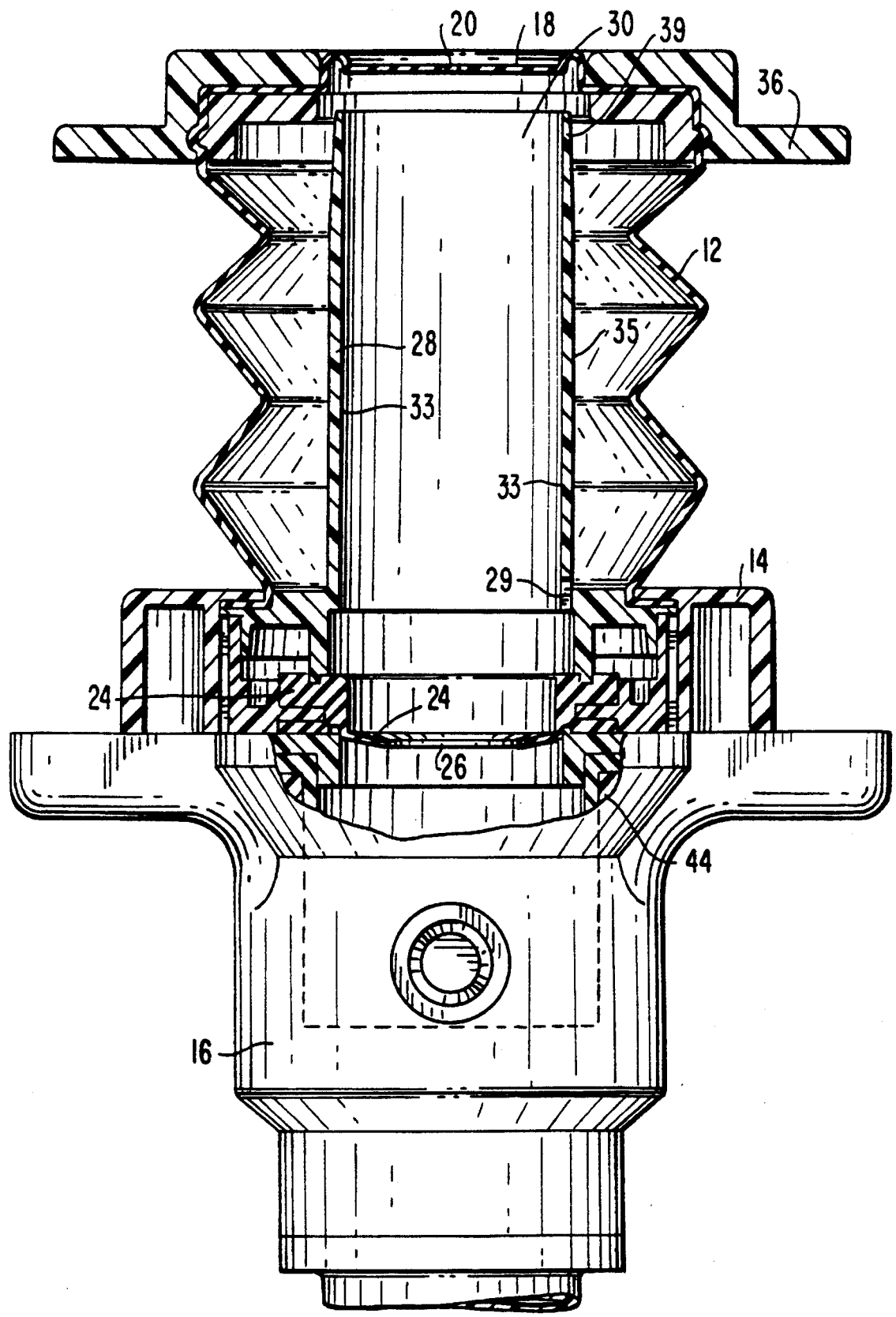
FIG. 3 is a partial cross-sectional view of the seal assembly illustrated in FIGS. 1 and 2 associated with the cannula assembly of FIG. 2A, which shows a seal member of the present invention in a non-dilated position.
Figure 4:
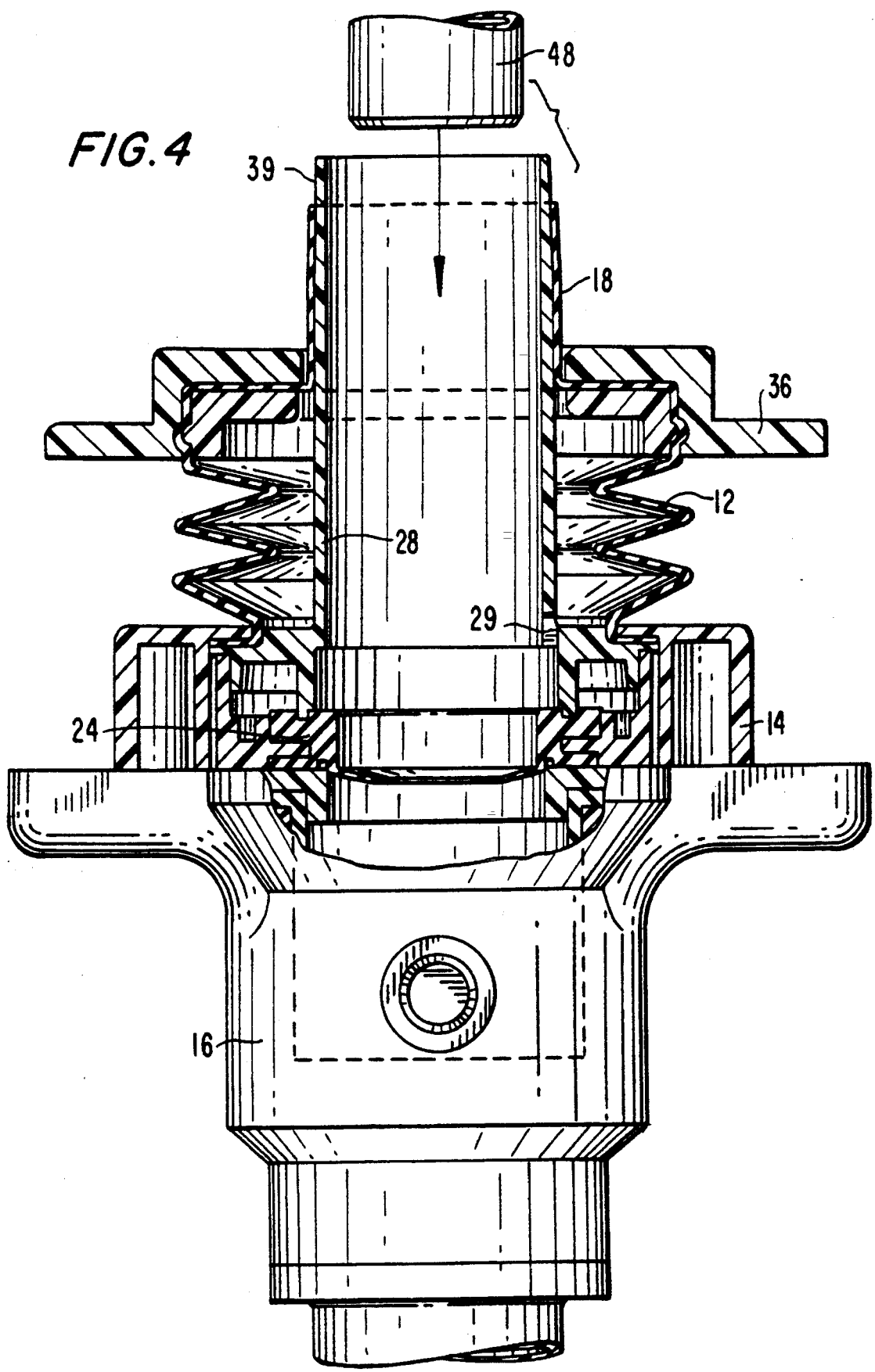
FIG. 4 is a partial cross-sectional view of the seal assembly similar to FIG. 3, except that the flange of the seal assembly is shown depressed so that the aperture of the seal member is dilated to the size of the opening of the dilator member.

The operation of seal assembly 10 in conjunction with cannula assembly 16 will now be described with reference to FIGS. 3 and 4. Prior to insertion of a surgical instrument, such as instrument 48, duckbill member 44 provides a fluid-tight seal to cannula assembly 16. Seal assembly 10 is mounted to cannula assembly 16 and is in a first or at-rest position with bellows 12 fully extended in the axial direction as shown in FIG. 3. In this position, seal assembly 10 can receive surgical instrumentation having a diameter which closely corresponds to the diameter of aperture 20 in gasket 18 with minimal insertion force required. Thus, if the diameter of aperture 20 is on the order of 4.5 mm, seal assembly 10 may receive surgical instruments of up to about 7 mm with minimal insertion force. However, with larger diameter instruments, e.g., instruments on the order of 10 to 12 mm in diameter, the insertion force required by the user with seal assembly 10 in the position shown in FIG. 3 increases substantially.

To reduce the force required to introduce such a larger diameter instrument 48 through aperture 20, flange 36 fabricated from a rigid polymeric material, e.g., ABS, is urged distally by the user, thereby translating gasket 18 with respect to dilator 28. This relative translation causes aperture 20 of gasket 18 to stretch around the inwardly tapered portion 39 of dilator 28, as shown in FIG. 4. This relative translation also causes bellows 12 to collapse and causes air egress through vent 29 into passage 30 of dilator 28, thereby preventing undesirable air compression in the region between dilator 28 and bellows 12 which would increase the force required to translate flange 36. As shown in FIG. 4, the resilience of gasket 18 allows distortion of a portion of gasket 18 to a substantially tubular orientation in conforming abutment with the outer face 35 of dilator 28. Instrument 48 can now be inserted through passage 30 within dilator 28 of seal assembly 10 and through cannula assembly 16 with minimal insertion force. Gasket member 24 and/or second gasket 49 sealingly engage instrument 48 as it passes therethrough. Thus, at the point instrument 48 passes through duckbill member 44, a fluid-tight seal within cannula assembly 16 and seal assembly 16 is nonetheless ensured by the interaction between instrument 48 and gasket member 24 and/or second gasket 49.

Once instrument 48 is inserted through dilator 28, flange 36 may be released by the user. Depending on the degree to which bellows 12 was collapsed and the degree of resilience of gasket 20 and bellows 12, bellows 12 may resume its initial at-rest position (as shown in FIG. 3) without further impetus by the user. However, if the forces exerted by gasket 20 and bellows 12 are insufficient to automatically return bellows 12 to its initial at-rest position, the user may raise flange 36 relative to cannula assembly 16, thereby inducing bellows 12 to resume its at-rest position. In either event, return of bellows 12 to its initial at-rest position allows gasket 18 to close around instrument 48, providing an ancillary fluid tight seal. The resilience of gasket 18 and the presence of convolution 19 advantageously facilitate some degree of axial movement of instrument 48 with respect to seal assembly 10 without any translation of instrument 48 with respect to gasket 18. Rather, gasket 18 retains a fixed arcuate line of contact with instrument 48 by resiliently deflecting with the movement of instrument 48, alternately assuming convex and concave orientations with the axial movement of instrument 48. Thus, the resilience of gasket 18 together with the presence of convolution 19 reduces the force required for limited movements of instrument 48, while also serving to stabilize instrument 48 within seal assembly 10 and cannula assembly 16.

A printed indicia, e.g., a transverse line, may be provided on outer face 35 of dilator 28 to indicate the point at which bellows 12 is sufficiently collapsed to prevent its automatic return to its initial at-rest position. Thus, if the user desires to utilize instrument 48 within the body cavity with seal assembly 10 in the position shown in FIG. 4, i.e., with bellows 12 in its collapsed position, the user may simply urge flange 36 distally to the extent necessary to move gasket 18 below the printed indicia on the outer face 35 of dilator 28.

If bellows 12 is returned to its initial at-rest position and it is desired to remove instrument 48 from cannula assembly 16 and seal assembly 10, the user may repeat the steps described hereinabove to expand the diameter of aperture 20, thereby facilitating passage of instrument 48 with minimal force. Similarly, if it is desired to remove a specimen from within the body cavity, the user may repeat the steps described hereinabove to expand the diameter of aperture 20 to facilitate specimen passage. The user may also, if desired and in the absence of a surgical instrument inserted therethrough, detach seal assembly 10 from cannula assembly 16 at any point during the surgical procedure to advantageously employ surgical instruments through the low profile cannula assembly provided according to the invention.

Figure 5:
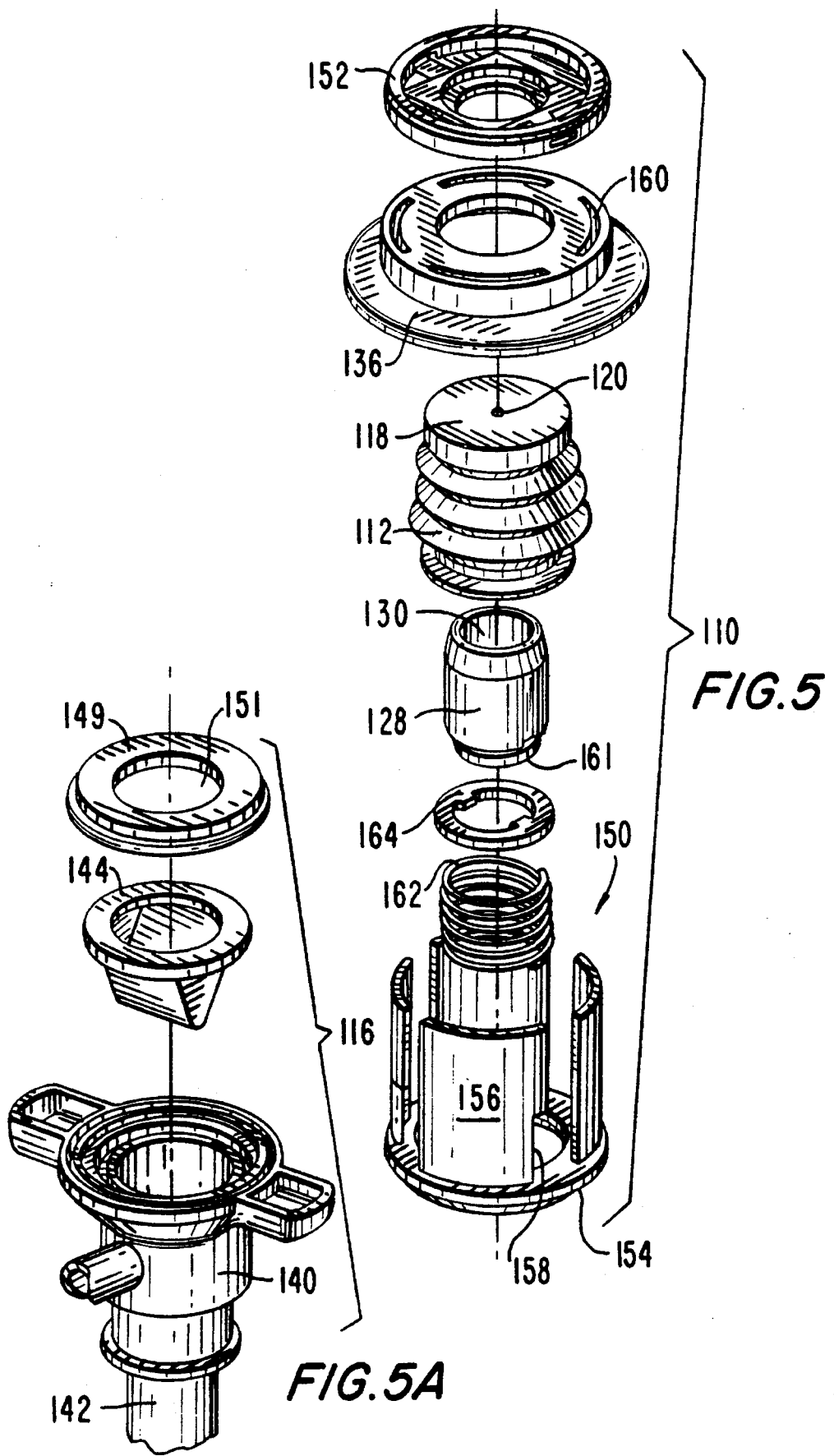
FIG. 5 is an exploded view with pans separated of another embodiment of the seal assembly of the present invention.
Figure 6:
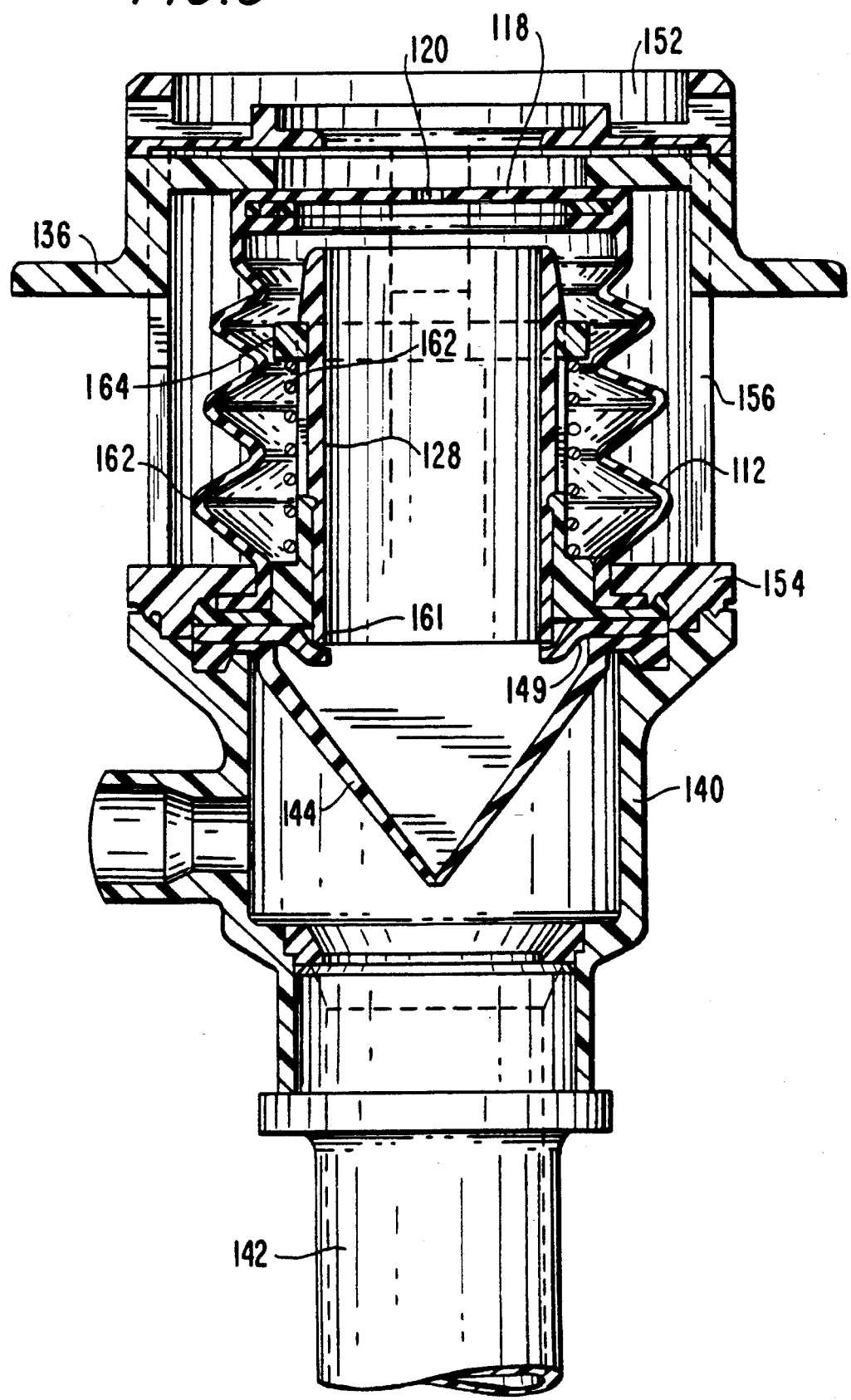
FIG. 6 is a partial cross-sectional view of the embodiment of FIG. 5, which shows a seal member of the embodiment in a non-dilated position.
Figure 7:
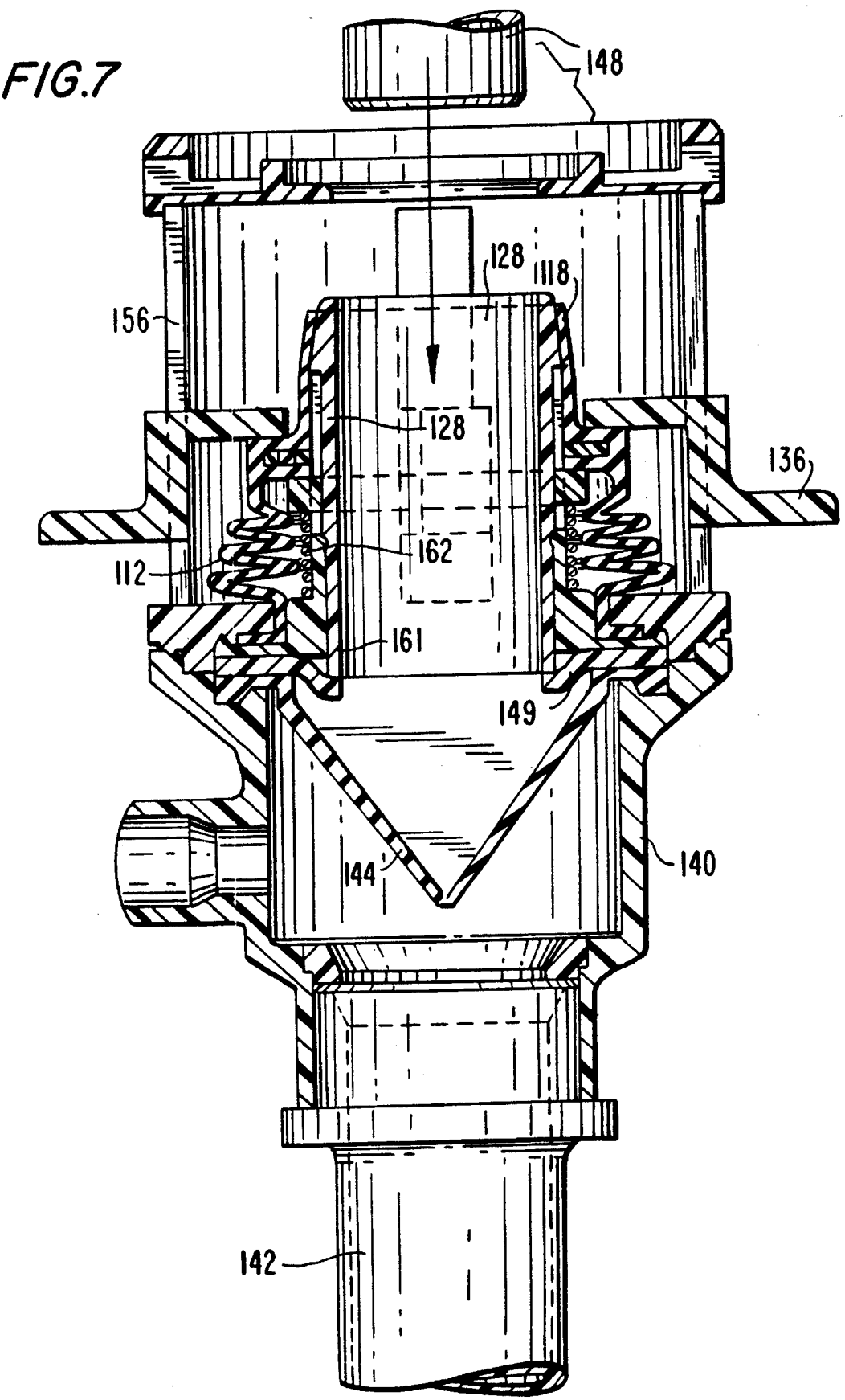
FIG. 7 is a partial cross-sectional view of the embodiment of FIG. 5, which shows the flange of the seal assembly depressed so that the aperture of the seal member is dilated to the size of the opening of the dilator member.

Another embodiment of the seal assembly of the present invention is illustrated in FIGS. 5–7. Seal assembly 110 is similar to seal assembly 10. Structures which are similar to structures in seal assembly 110 are designated with reference numerals similar to those of seal assembly 10 except a leading "1" has been added. With the exceptions noted below, operation of seal assembly 110, as shown in FIGS. 6 and 7, is as described in connection with seal assembly 10 and FIGS. 3 and 4 hereinabove.

Referring to FIGS. 5 and 5A, seal assembly 110 includes a rigid outer structure which comprises frame 150 which is preferably made of a ABS or a polycarbonate material. Frame 150 is in the form of a cage which is bounded at its proximal end by face 152 which is preferably bonded thereto, e.g., by an adhesive, sonic welding or the like. Frame 150 includes an annular base portion 154 to which dilator 128 is affixed, e.g., by an adhesive or sonic welding, and four rigid, proximally-directed arcuate portions 156, each having a notch 158 formed thereon. Flange 136 is provided with four arcuate slotted cut-outs 160 which may be cooperatively aligned with arcuate portions 156.

Dilator 128 includes a substantially tubular, distally-directed extension 161 which extends distally beyond the annular base portion 154 of frame 150. Extension 161 serves to dilate aperture 151 of gasket member 149 when seal assembly 110 is mounted to cannula assembly 116. The dilation of aperture 151 by extension 161 further reduces the force required to introduce an instrument therethrough. The presence of extension 161 on dilator 128 militates in favor of returning bellows 112 to its initial at-rest position after an instrument is inserted therethrough so that gasket 118 may sealingly engage the shaft thereof. In that regard, bellows 112 is biased proximally toward its initial at-rest position by spring 162 and beating ring 164.

When urged distally to collapse bellows 112 and expand aperture 120 of gasket 118 around dilator 128, flange 136 may be rotated clockwise, thereby locking flange 136 under notches 158 against the bias of spring 162, beating ring 164, and the :resilience of bellows 112 and gasket 118. The interaction between flange 136 and notches 158 of frame 150 provides an alternative means for maintaining bellows 112 in its collapsed position. As noted above, the retention of any bellows of the present invention in a collapsed configuration may be advantageous if it is desired to utilize a surgical instrument within the body cavity without the shaft of the instrument being engaged by the gasket (18, 118). With flange 136 locked under notches 158, aperture 120 is maintained in its expanded position around the exterior face 135 of dilator 128 until released by the user.

Figure 8:
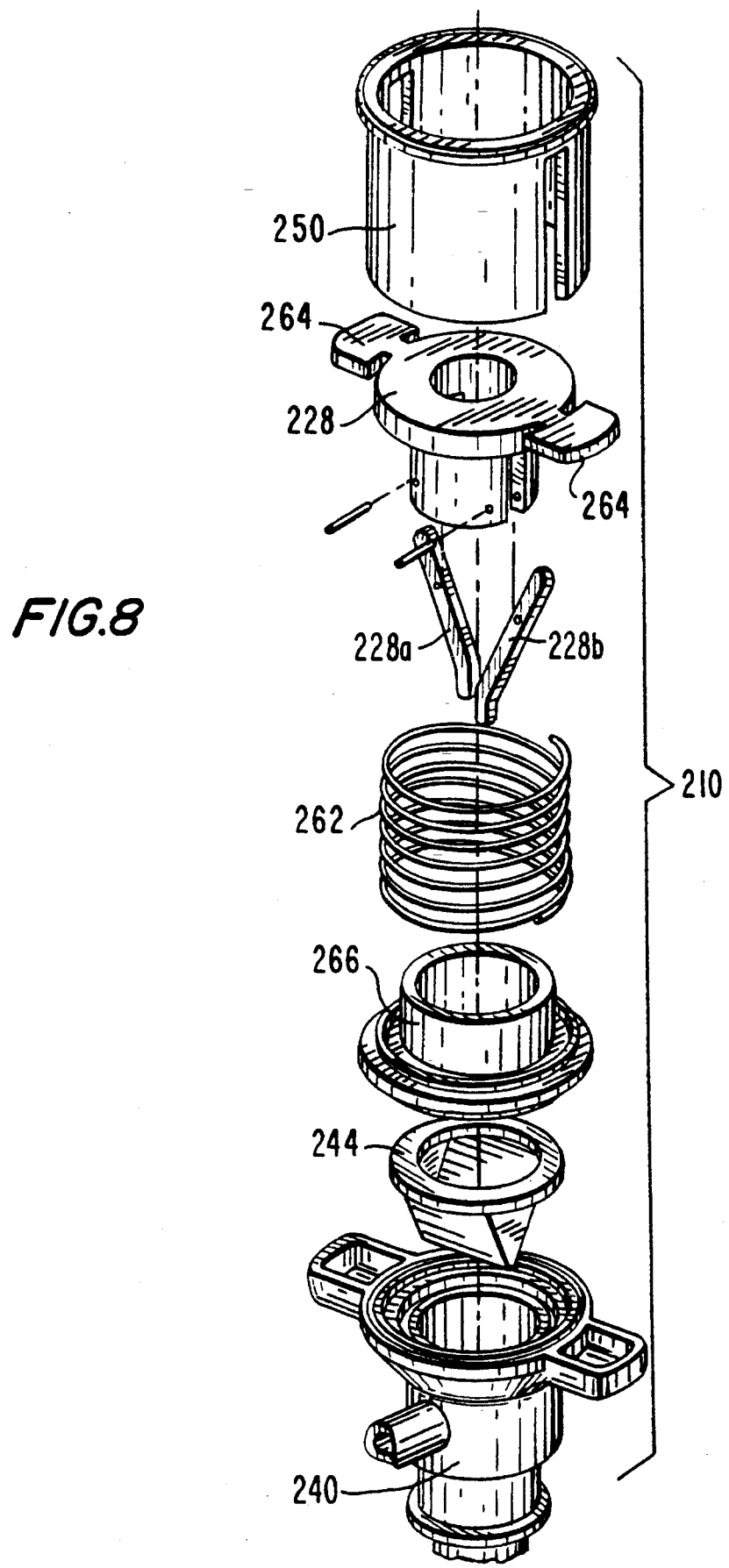
FIG. 8 is an exploded view with pans separated of another embodiment of the seal assembly of the present invention.
Figure 9:
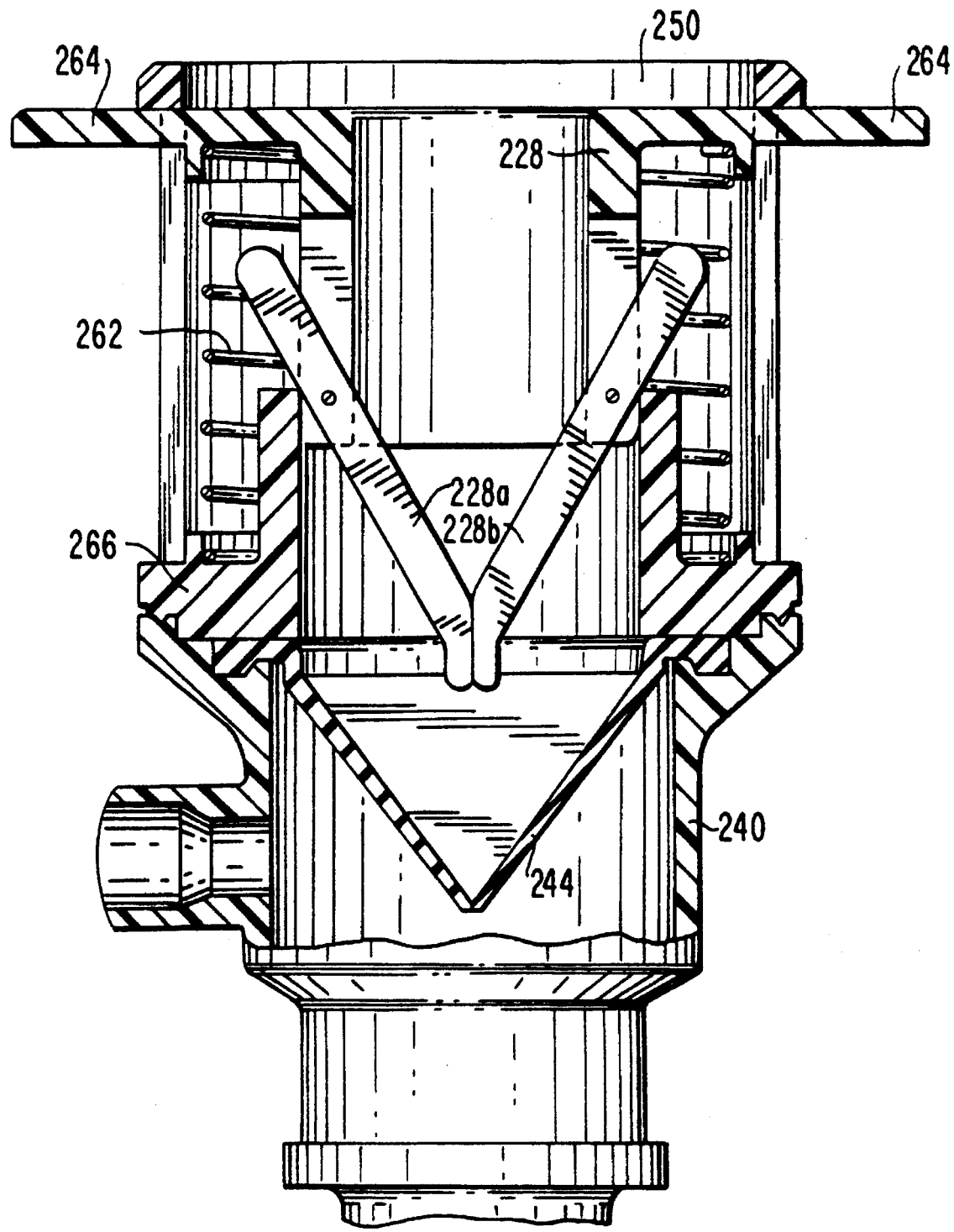
FIG. 9 is a partial cross-sectional view of the embodiment of FIG. 8, which shows a seal member of the embodiment in a non-dilated position.
Figure 10:
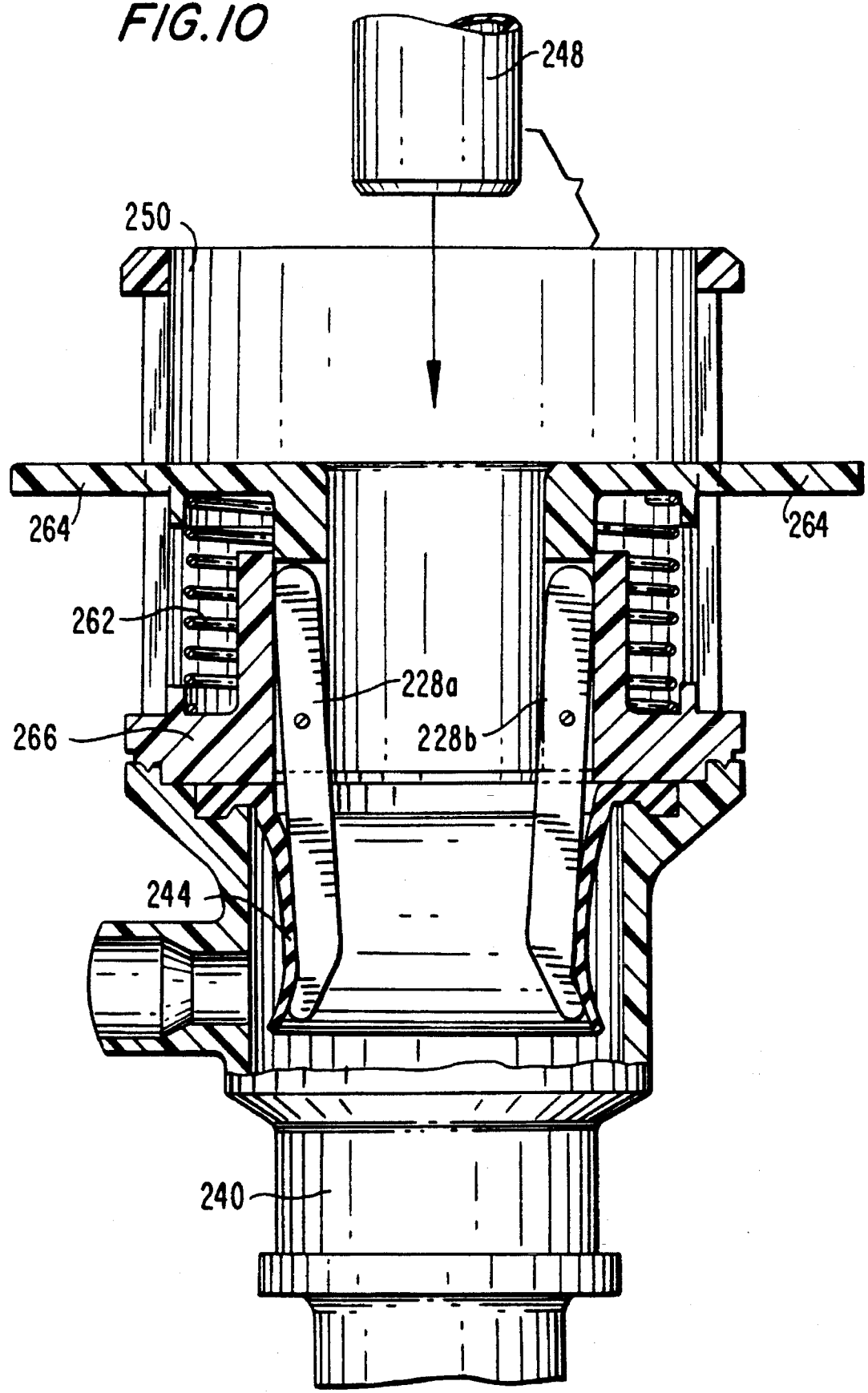
FIG. 10 is a partial cross-sectional view of the embodiment of FIG. 8, which shows the flange of the seal assembly depressed so that the aperture of the seal member is dilated by the pivoting dilator members.

Another embodiment of the seal assembly of the present invention is illustrated in FIGS. 8–10 as seal assembly 210 which is similar in certain respects to seal assemblies 10 and 110. Structures which are similar to corresponding structure in seal assemblies 10 and 110 are designated by the same numerals except that a leading "2" has been added for clarity and consistency.

In seal assembly 210, dilator 228 is movable relative to duckbill 244 which performs the assembly's sealing function. Other seal members may be provided in addition to or in place of duckbill 244, as for example, one or more gaskets as described hereinabove. Dilator 228 is provided with extended members 228a and 228b pivotably mounted thereto and tab portions 264 to facilitate movement of dilator 228 in a distal direction. Dilator 228 is biased in a proximal direction by spring 262 which bears against collar 266. Collar 266 also serves as a camming surface for extended members 228a and 228b during distal motion of dilator 228 as best be seen in FIGS. 9 and 10.

In operation, as illustrated in FIGS. 9 and 10, when it is necessary or desirable to insert a large diameter instrument, e.g., an instrument having a diameter on the order of 7 to 15 mm, dilator 228 is moved distally by advancing tabs 264 relative to cannula assembly 240. Extended members 228a and 228b contact collar 266 and are cammed thereby so that extended members 228a and 228b pivot to spread open the slit of duckbill 244 as illustrated in FIG. 10. Instrument 248 is then inserted through seal assembly 210 and tab portions 264 are released to allow duckbill 244 to close around instrument 248. As noted above, other seal configurations may be readily used to supplement or replace duckbill 244. For example, a planar seal member having a central aperture or slit may be utilized in which event extended members 228a and 228b will serve to expand the size of the aperture or slit in the same manner as described for expanding the slit of duckbill 244.

Figure 11:
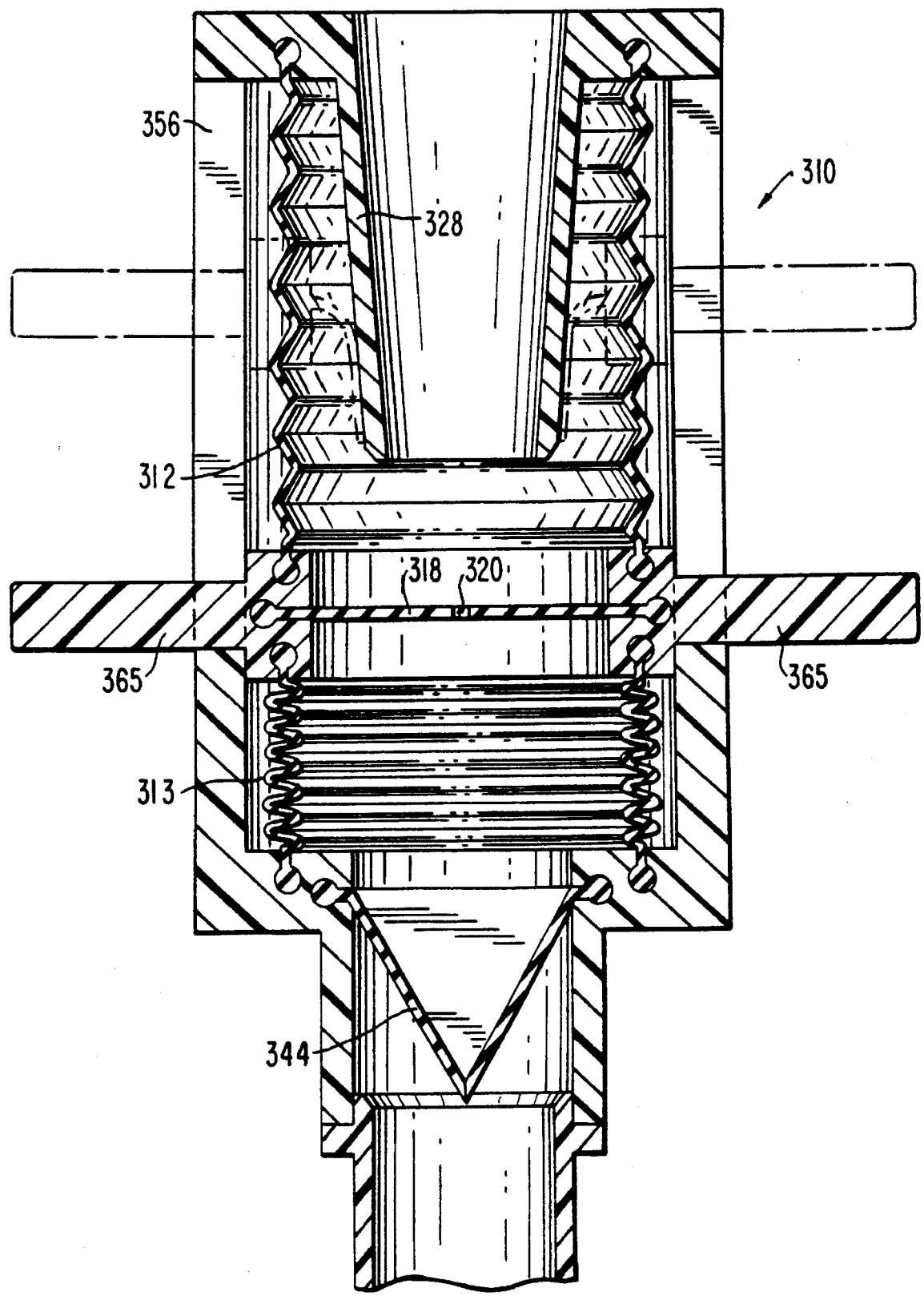
FIG. 11 is a cross-sectional view of another embodiment of the seal assembly of the present invention.

Another embodiment of the seal assembly of the present invention is illustrated in FIG. 11 as seal assembly 310 which is most closely related in structure and operation to seal assembly 110 of FIGS. 5–7, described above. Seal assembly 310 differs from seal assembly 110 in that dilator 328 is conical and is fixed with respect to the frame 356. Gasket 318 is positioned distally of dilator 328 when seal assembly 3 10 is in its initial at-rest position and is adapted for axial movement with respect thereto. Additional bellows 313 is secured to seal carrier flange 365 at its proximal end and to the distal portion of frame 356 so as to form a fluid-fight passageway therewithin. In order to dilate aperture 320 of seal 318, seal carrier flange 365 is pulled proximally as shown in phantom lines in FIG. 11, thereby translating gasket with respect to dilator 328 and expanding aperture 320 therearound. Proximal translation of seal carrier flange serves to collapse bellows 312 while simultaneously axially extending additional bellows 313.

Figure 12:
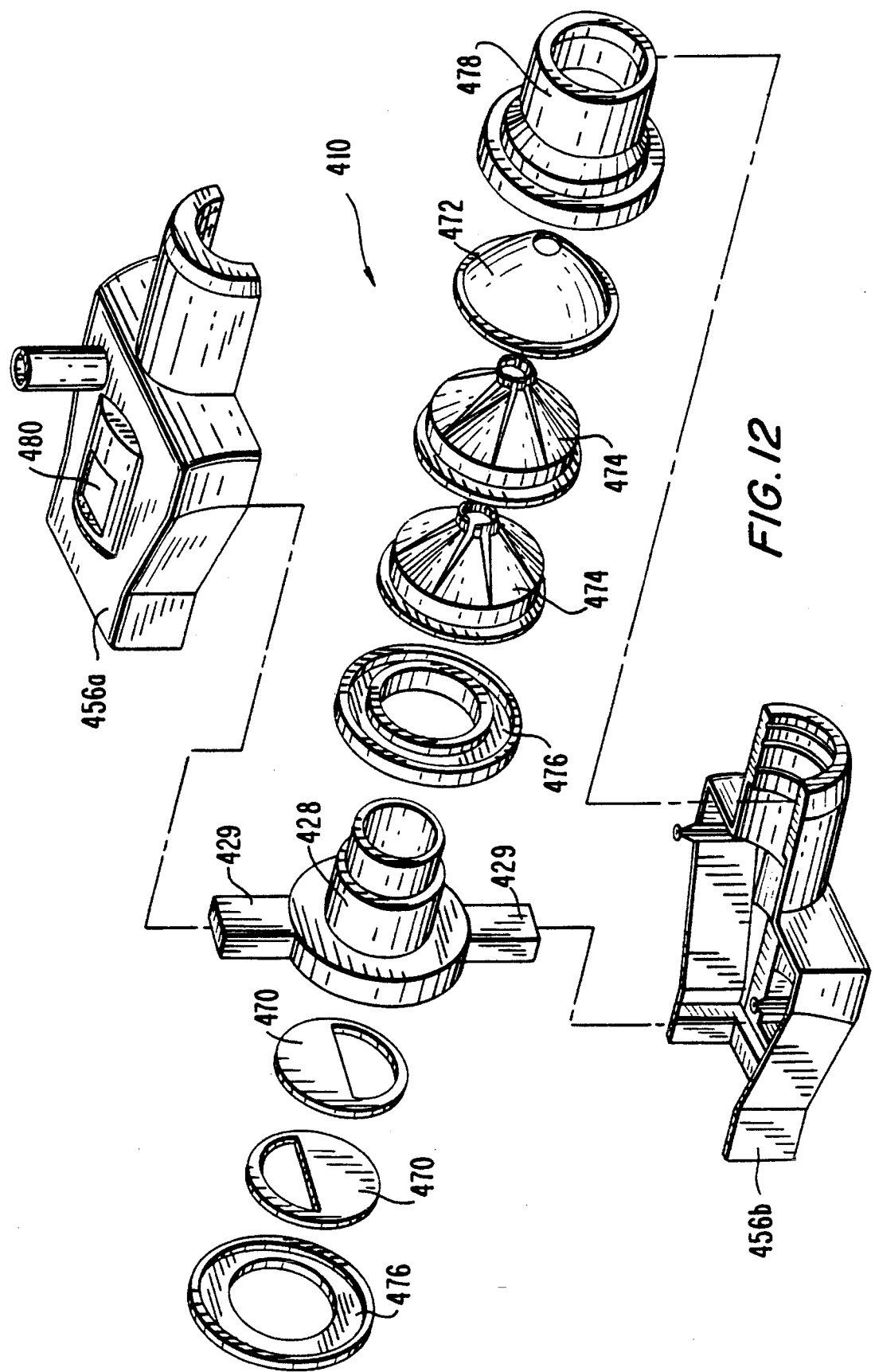
FIG. 12 is an exploded view with parts separated of another embodiment of the seal assembly of the present invention.

Another embodiment of the seal assembly of the present invention is illustrated in FIGS. 12 to 14 as seal assembly 410 which is incorporated in cannula housing sections 456a and 456b. A plurality of sealing elements such as overlapping sealing members 470 and conical gasket 472 are provided, as well as reinforcing and penetration prevention means such as conical members 474 which include overlapping tab portions for spreading and protecting gasket 472. Members 476, preferably of an elastomeric material, are provided to substantially seal the interior passageway formed by the tubular extension of cannula housing sections 456a and 456b. Collar member 478 is provided and adapted for attachment to the distal end of cannula housing sections 456a and 456b.

Dilator 428 includes ears 429 which extend through windows 480 formed in cannula housing sections 456a and 456b. When the surgeon desires to introduce an instrument of relatively large diameter, the surgeon may advance ears 429 and thus dilator 428 relative to cannula housing 456. Conical members 474 and gasket 472 which are positioned distal to dilator 428 are fixed with respect to cannula housing 456 and, therefore, distal movement of dilator 428 serves to dilate elements 474 and conical gasket 472.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A seal assembly which comprises:

(a) a housing;

(b) a resilient first gasket associated with said housing, said first gasket having an aperture formed therein for receiving surgical instrumentation; an, (c) dilating means forming a passageway therethrough and having a continuous exterior face of fixed dimension associated with said housing for dilating said aperture of said first gasket;

wherein said first gasket and said dilating means are adapted for relative movement therebetween, said first gasket and said dilating means assuming a first position wherein said aperture of said first gasket is spaced from said dilating means and is adapted to receive surgical instrumentation of a first diameter with minimal insertion force, and assuming a second position wherein said aperture of said first gasket is stretched around said exterior face of said dilating means for receiving surgical instrumentation of a second diameter greater than said first diameter with minimal insertion force.

2. The seal assembly of claim 1, wherein said housing is adapted to be associated with a cannula assembly.

3. The seal assembly of claim 2, wherein said cannula assembly includes seal means which is configured and dimensioned to provide a fluid-tight seal in the absence of an instrument passing therethrough.

4. The seal assembly of claim 3, wherein said seal means comprises a distally directed duckbill member.

5. The seal assembly of claim 1, wherein said first gasket is substantially planar and is mounted transverse with respect to said housing.

6. The seal assembly of claim 1, wherein said first gasket is fixedly attached with respect to said housing.

7. The seal assembly of claim 1, wherein said dilating means is fixedly attached to said housing.

8. The seal assembly of claim 1, wherein said housing comprises a bellows.

9. The seal assembly of claim 8, wherein said bellows is adapted, to assume an extended position which corresponds to said first position of said first gasket and said dilating means, and a collapsed position which corresponds to said second position of said first gasket and said dilating means.

10. The seal assembly of claim 8, wherein said bellows is encased within a frame.

11. The seal assembly of claim 10, wherein said frame further comprises a flange associated with said bellows for moving said bellows between said extended position and said collapsed position.

12. The seal assembly of claim 8, further comprising biasing means for biasing said bellows to said extended position.

13. A seal assembly which comprises:

(a) a housing;

(b) resilient first seal means associated with said housing, said first seal means having an aperture formed therein for receiving surgical instrumentation; and (c) dilating means forming a passageway of fixed dimension therethrough and associated with said housing for dilating said aperture of said first seal means;

wherein said first seal means and said dilating means are adapted for relative movement therebetween, said first seal means and said dilating means assuming a first position wherein said aperture of said first seal means is spaced from said dilating means and is adapted to receive surgical instrumentation of a first diameter with minimal insertion force, and assuming a second position wherein said aperture of said first seal means is stretched by said dilating means, for receiving surgical instrumentation of a second diameter greater than said first diameter with minimal insertion force.

14. A seal assembly according to claim 13, wherein said dilating means includes a dilator member slidably mounted relative to said housing.

15. A seal assembly as in claim 14, wherein said dilating means includes a pair of elongated members pivotably attached to said dilator member and extending therefrom such that upon sliding movement of said dilator member, said pair of elongated members pivot and contact said first sealing member, thereby causing said aperture to expand from said first position to said second position.

16. The seal assembly of claim 13, wherein said housing is adapted to be associated with a cannula assembly.

17. The seal assembly of claim 16, wherein said cannula assembly includes a second seal means.

18. The seal assembly of claim 17, wherein said second seal means comprises a distally directed duckbill member.

19. The seal assembly of claim 13, wherein said first seal means comprises a substantially planar gasket mounted transverse with respect to said housing.

20. The seal assembly of claim 13, wherein said first seal means is fixedly attached with respect to said housing.

21. The seal assembly of claim 13, further comprising biasing means operatively associated with said dilating means for biasing said dilating means to said first position.

22. A seal assembly which comprises:

(a) a housing;

(b) a seal member associated with said housing, said seal member having an aperture formed therein for receiving surgical instrumentation; and (c) an elongated tubular dilator member operatively associated with said seal member;

wherein said seal member and said elongated tubular dilator are adapted for relative movement therebetween, said seal member and said elongated tubular dilator member assuming a first position wherein said aperture of said seal member is spaced from said elongated tubular dilator and is adapted to receive surgical instrumentation of a first diameter with minimal insertion force, and assuming a second position wherein said aperture of said seal member is stretched by said elongated dilator member to receive surgical instrumentation of a second diameter greater than said first diameter with minimal insertion force.

* * * * *